US010820648B2

(12) United States Patent
Hoffman et al.

(10) Patent No.: US 10,820,648 B2
(45) Date of Patent: Nov. 3, 2020

(54) METHOD FOR TAILORING A COMPRESSION GARMENT

(71) Applicant: SIGVARIS AG, St. Gallen (CH)

(72) Inventors: Keith A. Hoffman, Hudsonville, MI (US); Laure Kuipers, Holland, MI (US)

(73) Assignee: Sigvaris AG, St. Gallen (CH)

( * ) Notice: Subject to any disclaimer, the term of this patent is extended or adjusted under 35 U.S.C. 154(b) by 230 days.

(21) Appl. No.: 15/808,092

(22) Filed: Nov. 9, 2017

(65) Prior Publication Data

US 2019/0133229 A1 May 9, 2019

(51) Int. Cl.
| A61F 13/08 | (2006.01) |
| A41H 1/02 | (2006.01) |
| A61H 1/00 | (2006.01) |
| A41H 1/06 | (2006.01) |

(52) U.S. Cl.
CPC ................. *A41H 1/02* (2013.01); *A41H 1/06* (2013.01); *A61F 13/085* (2013.01); *A61H 1/006* (2013.01); *A61H 2201/0192* (2013.01); *A61H 2201/164* (2013.01); *A61H 2205/106* (2013.01)

(58) Field of Classification Search
CPC .... A61F 13/0273; A61F 13/08; A61F 13/085; A61F 2013/0028; A61H 1/006; A61H 2201/0192; A61H 2201/164; A61H 2205/106
See application file for complete search history.

(56) References Cited

U.S. PATENT DOCUMENTS

| 4,215,687 A | 8/1980 | Shaw |
| 5,108,455 A * | 4/1992 | Telikicherla ............... A61F 2/60 623/27 |
| 5,254,122 A | 10/1993 | Shaw |
| 5,906,206 A | 5/1999 | Shaw et al. |
| 8,801,645 B2 * | 8/2014 | Lipshaw ............... A61F 13/085 602/75 |

(Continued)

FOREIGN PATENT DOCUMENTS

| WO | 2014/116497 A1 | 7/2014 |
| WO | 2016/048827 A1 | 3/2016 |

OTHER PUBLICATIONS

ManMade. "The DIY Tailor: How to Hem Jeans Like a Pro". URL="https://www.manmadediy.conn/2617-the-diy-tailor-how-to-hem-jeans-like-a-pro". Accessed Jun. 10, 2020. Published Oct. 11, 2016. (Year: 2016).*

*Primary Examiner* — Jameson D Collier
(74) *Attorney, Agent, or Firm* — McCormick, Paulding & Huber PLLC

(57) ABSTRACT

A method for tailoring a compression garment including a first sheet and a second sheet, each having a first lateral end and a second lateral end, at least one strap for holding together the first lateral end of the first sheet and the first lateral end of the second sheet. The strap is tightenable to establish a compression level to a human limb or body part. The method includes: adjusting the strap; draping the compression garment around the limb or the body part; holding the second lateral end of the first sheet and the second lateral end of the second sheet together to pull the first sheet, the second sheet and the strap into contact with the limb or body part; marking a cutting line on one or both sheets; cutting the sheets along the cutting line; and splicing together both cut ends with at least one splicing element.

26 Claims, 3 Drawing Sheets

(56) References Cited

U.S. PATENT DOCUMENTS

| | | |
|---|---|---|
| 9,642,766 B2 * | 5/2017 | Lipshaw .............. A61H 1/008 |
| 2002/0062096 A1 | 5/2002 | Bennett |
| 2005/0192524 A1 | 9/2005 | Lipshaw et al. |
| 2010/0312160 A1 | 12/2010 | Creighton et al. |
| 2012/0179084 A1 | 7/2012 | Lipshaw et al. |
| 2015/0025424 A1 | 1/2015 | Richardson et al. |
| 2016/0166458 A9 | 6/2016 | Lipshaw et al. |

* cited by examiner

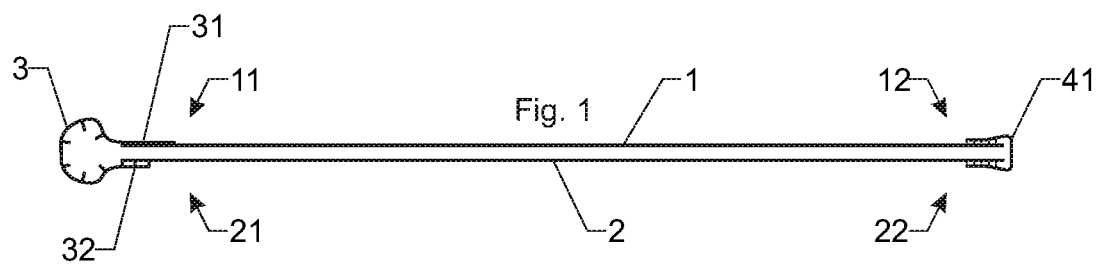
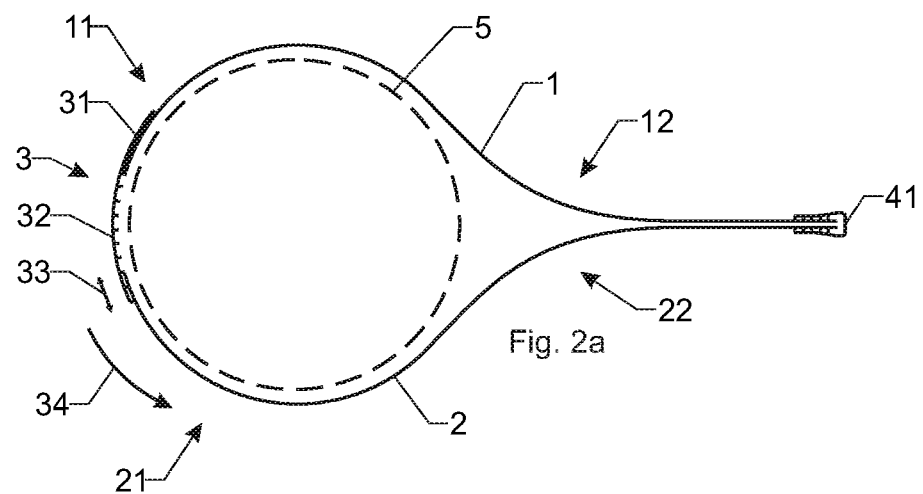
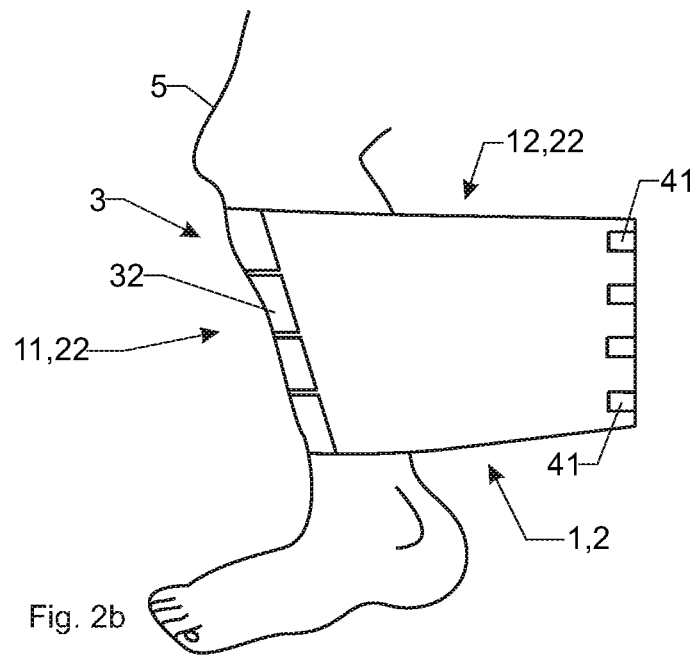

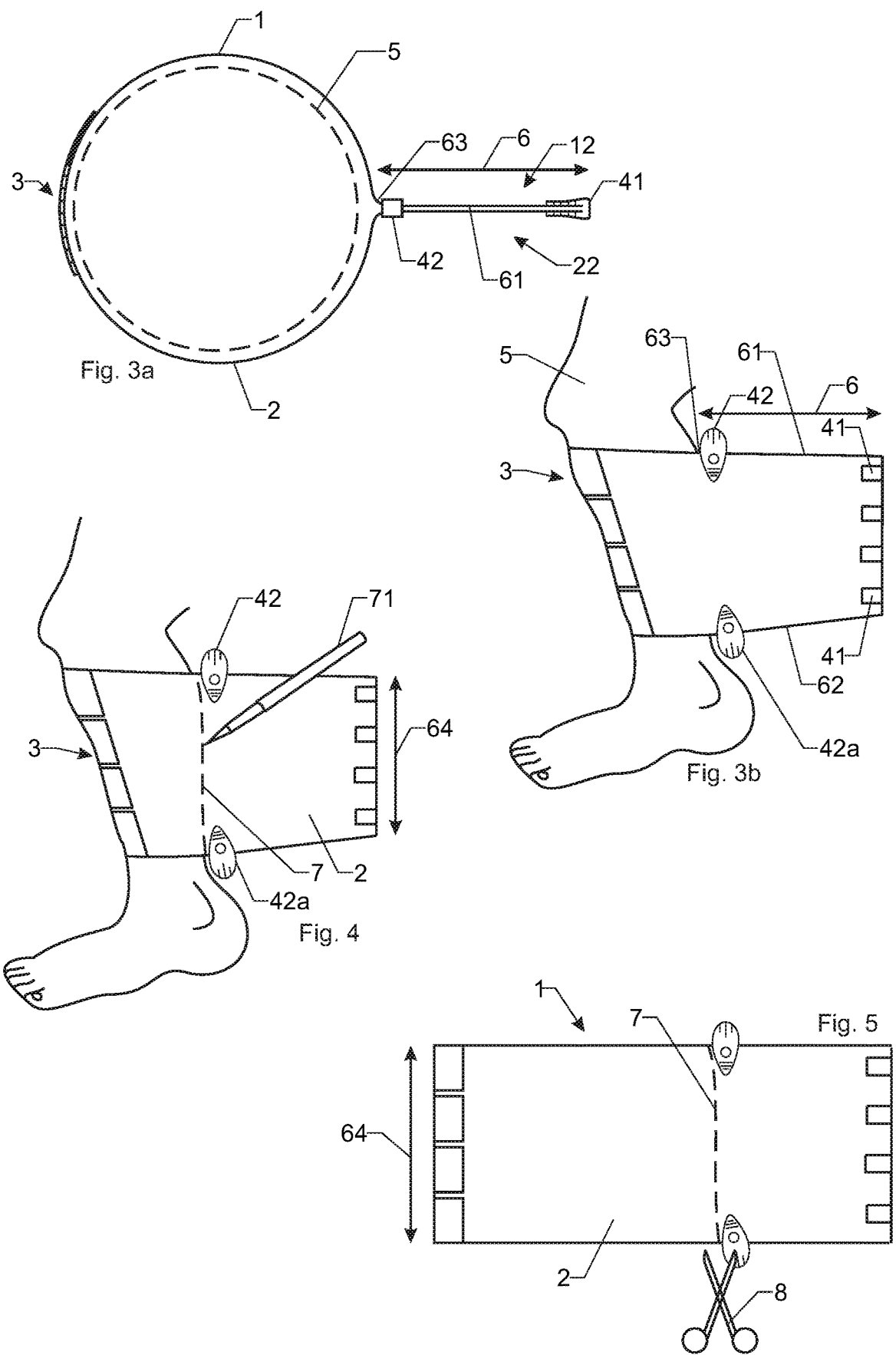

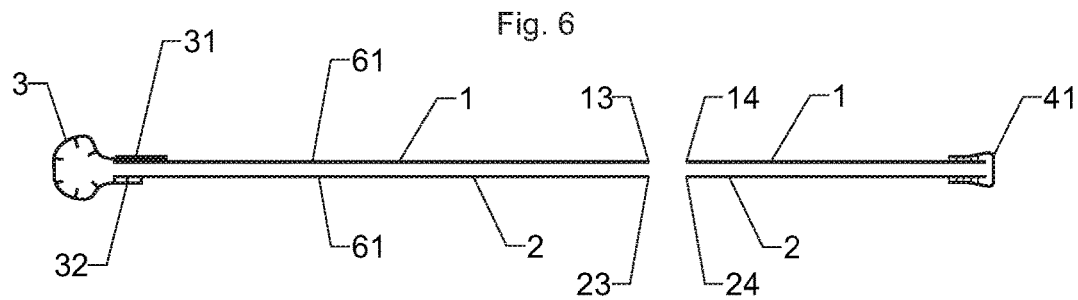
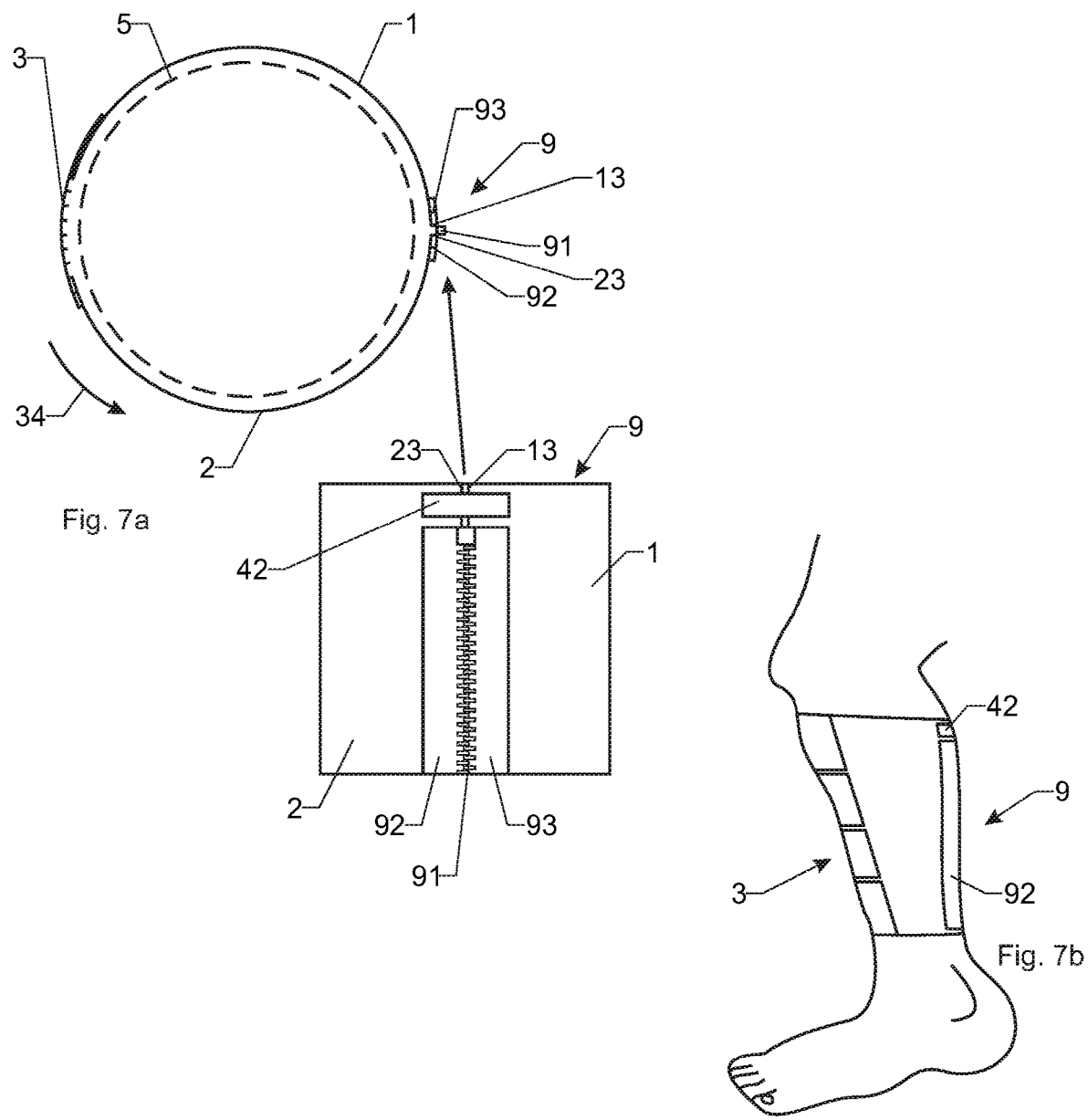

METHOD FOR TAILORING A COMPRESSION GARMENT

TECHNICAL FIELD

This invention relates to a method for tailoring a compression garment. The compression garment comprises a first sheet and a second sheet, each having a first lateral end and a second lateral end. Furthermore, the compression garment comprises at least one strap for holding together the first lateral end of the first sheet and the first lateral end of the second sheet, wherein said at least one strap is tightenable to establish a compression level to a human limb or body part by the compression garment. The invention further relates to a compression garment kit.

BACKGROUND ART

Edema may arise from a variety of illnesses and conditions, including venous valvular insufficiency, postphlebotic syndrome, and lymphedema. Compression methods control edema by reducing interstitial fluid.

Due to considerable variation in limb shapes and sizes, custom garments may typically be required. To facilitate the manufacture of these garments, various partially fabricated kits are available for a therapist or fitter to customize and fit a patient. Typical compression garment kits require measuring the patient to indicate cutting locations on the compression garment, in a manner that takes time and provides limited accuracy. The position of the measurement on the patient may not exactly align with the location marked on the garment, and typically only two or three measurements are transferred to the garment.

Compression garments supplied in kit form known in the art either do not provide a contoured shape to precisely fit the body part or limb, or the process for assembling the contoured shape is very tedious.

SUMMARY

It is an object of the invention to provide a method for easily and quickly tailoring a compression garment to a patient.

This object is met by a method for tailoring a compression garment, said compression garment comprising
 a first sheet and a second sheet, each having a first lateral end and a second lateral end,
 at least one strap for holding together the first lateral end of the first sheet and the first lateral end of the second sheet, wherein said at least one strap is tightenable to establish a compression level to a human limb or body part by the compression garment,
 the method including:
 a first step of adjusting the at least one strap to a first position, preferably to be in position providing the largest extension of the at least one strap;
 a second step of draping the compression garment around the limb or the body part;
 a third step of holding the second lateral end of the first sheet and the second lateral end of the second sheet together to pull the first sheet, the second sheet and the at least one strap into contact with said limb or body part;
 a fourth step of marking a cutting line on one or both sheets;
 a fifth step of cutting the first and the second sheet along the cutting line; and
 a sixth step of splicing together both cut ends with at least one splicing element.

After having tailored the compression garment, the patient can tighten the straps in order to establish a compression to the human limb or body part.

The first step of adjusting the at least one strap can be performed by the patient or an auxiliary person. Alternatively, the first step can be performed by the manufacturer such that the straps are already correctly adjusted when the patient buys the product.

The third step can be performed by the patient or the auxiliary person by holding the first sheet and the second sheet together by hand or by a fixation element, for example. The term "second lateral end" is broadly understood. The "second lateral end" comprises all positions between the edges of the sheets and the position where the sheets start surrounding the human limb or body part. This understanding will be further explained by the description of the drawings.

The disclosed method enables the patient or an auxiliary person to easily and quickly tailor the compression garment to the individual shape and size of the patient's body part or limb. A method for custom fitting a compression garment is disclosed whereby no measurements of the patient are required to tailor a garment that is easy to assemble and fits the contour of a patient's limb or body part. Furthermore, the compression garment is appropriate for use where reduction in edema is anticipated, as it can easily be trimmed to fit a smaller body size after the edema has been reduced by the disclosed method.

The at least one strap of the compression garment provided to securing the garment in the compression state may be of the hook and loop type, or known as VELCRO® fasteners, or may comprise or include other known fastening means.

By a preferred embodiment of the method, the second lateral end of the first sheet and the second lateral end of the second sheet are held together, in particular by at least one temporary releasable fixation element, such that the lateral edges of the first sheet and of the second sheet are aligned.

If the lateral edges are aligned, the patient or the auxiliary person only needs to mark one sheet of the garment and can cut both sheets at the same time. If the edges are not aligned, one would have to mark both sheets of the garment when tailoring, and cut the two sheets independently. Furthermore, if the edges are not aligned, the first sheet and the second sheet might not have the same size and the straps might not be centered on the compression garment.

By a further preferred embodiment of the method, the second lateral end of the first sheet and the second lateral end of the second sheet are held together by arranging at least one fixation element at a top end and/or at a bottom end at the most inner meeting point of the second lateral end of the first sheet and the second sheet, and/or by arranging at least one fixation element at the lateral edges of the second lateral ends of the first sheet and the second sheet.

It is preferred that the second lateral end of the first sheet and the second lateral end of the second sheet are held together by arranging at least one fixation element directly at said limb or body part or with a small distance from said limb or said body part, preferably with a distance of at most 3 cm or at most 1 cm or at most 0.5 cm, on said lateral ends opposite to the straps. "Directly" means that the fixation element is arranged as close to the limb or the body part as possible with the normal strength of a human.

Advantageously, the splicing element comprises a slide fastener, in particular a zip fastener.

Furthermore, at the sixth step both cut ends might additionally be spliced together by the fixation element.

The exact length of the cut ends will vary, as the compression garment can be cut down in length and the cut ends are curved in shape. Since it is not desired to cut the splicing element, in particular the zip fastener, it is designed to be shorter in length than the cut ends. At least one fixation element, which has already been used for holding the sheets together while marking and cutting the sheets might be placed adjacent to the splicing element as an additional splicing element.

By a preferred embodiment, the splicing element is attached on the first sheet and on the second sheet by hook-and-loop fasteners, known as VELCRO®.

A strip of a hook surface might be sewn to each side of the zip fastener, and the strips are attached to the hook receptive surface of the garment.

Advantageously, the cutting line is marked on the garment
  directly at said limb or body part opposite to the straps, or
  with a small distance from the limb or the body part,
    preferably with a distance of at most 3 cm or at most 1 cm or at most 0.5 cm opposite to the straps, or
  where the first sheet and the second sheet meet opposite to the straps at the position closest to the limb or the body part.

Furthermore, a cumulated length of the first sheet and the second sheet and the at least one strap might be longer than a circumference of said limb or body before tailoring the compression garment.

By a preferred embodiment the first sheet and the second sheet extend to the full longitudinal length of the compression garment wherein the longitudinal length of the sheets is perpendicular to the lateral length of the sheets.

By a further preferred embodiment, the method comprises a further step before the first step, wherein the compression garment is pre-cut to get the size of the compression garment closer to the size of the limb before precisely tailoring the compression garment.

Furthermore, the fixation element might be a spring loaded clip.

It is another object of the invention to provide a compression garment kit that allows an easy and quick tailoring of the compression garment.

This object is met by a compression garment kit which comprises a compression garment with
  a first sheet and a second sheet, each having a first lateral end and a second lateral end,
  at least one strap for holding together the first lateral end of the first sheet and the first lateral end of the second sheet, wherein said at least one strap is tightenable to establish a compression level to a human limb or body part by the compression garment, and
  a splicing element for holding together the second lateral end of the first sheet and the second lateral end of the second sheet.

The compression garment comprises an additional fixation element for temporarily holding together the first sheet and the second sheet.

Advantageously, the first sheet and the second sheet extend to the full longitudinal length of the compression garment.

BRIEF DESCRIPTION OF THE DRAWINGS

The above and other features and advantages of the present invention will become more apparent to those of ordinary skill in the art by describing in detail preferred embodiments thereof with reference to the attached drawings in which:

FIG. 1 shows a schematic top view of a compression garment in an initial unwrapped state before tailoring the compression garment;

FIG. 2a shows a top view and FIG. 2b a side view of a compression garment after draping the compression garment around a leg;

FIG. 3a shows a top view and FIG. 3b a side view of a compression garment, wherein the first sheet and the second sheet are held together by several fixation elements;

FIG. 4 shows a side view of a compression garment illustrating the fourth step of marking a cutting line on one of the two sheets;

FIG. 5 shows a side view of a compression garment illustrating the fifth step of cutting the first and the second sheet along the cutting line;

FIG. 6 shows a schematic top view of a compression garment wherein the first sheet and the second sheet are cut open in two pieces; and FIGS. 7a and 7b show a compression garment wherein both cut ends of the first sheet and the second sheet are spliced together by a zip fastener.

DETAILED DESCRIPTION

An example of the method and of a compression garment kit according to the invention are now described in more detail with reference to FIGS. 1 to 7. The compression garments are made from the usual materials used for manufacturing compression garments. Such materials are known to the skilled person. In particular, the materials are different kinds of textiles which can be said as being elastic textiles or inelastic textiles within the range of forces that occur during the use of compression garments. Accordingly, the compression garments may be made of elastic materials only or may be made of inelastic materials only, or such garments may be made from a combination of elastic and inelastic materials, in particular textiles. The textiles or other materials forming together the compression garments may be connected to each other by sewing, laminating, bonding, by adhesives or glues, or by other methods or means known to the skilled person.

In FIG. 1 an example of an unwrapped compression garment is shown in a top view. The compression garment comprises a first sheet 1 and a second sheet 2. The first sheet 1 comprises a first lateral end 11 and a second lateral end 12. The second sheet 2 comprises a first lateral end 21 and a second lateral end 22.

The first lateral ends 11 and 21 are held together by several straps 3. The straps 3 are connected to the first lateral end 11 of the first sheet 1 by a seam 31 and to the first lateral end 21 of the second sheet 2 by a hook and loop fastener 32 which are known as VELCRO®-fasteners. Alternatively, the straps could alternate with the first strap sewn to the first sheet 1, the second strap sewn to the second sheet 2, the third strap sewn to the first sheet 1, and so forth. The inner surface of the straps 3 comprises a hook layer and the outer surface of the second sheet 2 comprises a loop layer. The straps are adjustable to establish and adjust the compression during the use of the compression garment.

The second lateral ends 12 and 22 are held together by several temporary releasable fixation elements 41. The fixation elements 41 may be connected to the second lateral ends 12 and 22 by a hook and loop fastener, as shown in the figures, or any other releasable fixing means, such as a spring loaded clip.

In FIGS. 2a and 2b the compression garment is draped around the leg 5 such that it is pulled into contact with the limb. The first lateral ends 11 and 21 are arranged at the front side of the leg, at the shin, or at the lateral and medial sides of the leg, and the second lateral ends 12 and 22 are arranged at the back side of the leg.

The straps 3 are in a first position providing the largest extension of the at least one strap 3. With other words, the overlap 33 between the strap 3 and the second sheet 2 is as small as possible such that the straps 3 can be tightened in the direction of the arrow 34 in order to establish compression to the leg.

In FIGS. 3a and 3b the second lateral end 12 of the first sheet 1 and the second lateral end 22 of the second sheet 2 are held together by temporary releasable fixation elements 41 and 42 while pulling the first sheet 1, the second sheet 2, and the at least one strap 3 against the leg. Preferably, enough tension will be applied to pull the first sheet 1, the second sheet 2, and the at least one strap 3 into conformity with the shape of the limb. This corresponds to the third step according to the disclosed method. The fixation elements 41 and 42 can have the same or different size and shape. In the exemplary embodiment of the figures, the fixation elements 41 are hook and loop fasteners and the fixation element 42 is a spring loaded clip.

The second lateral ends 12 and 22 of the sheets 1 and 2 are understood to comprise the whole section on the back side of the leg 5 as indicated by the arrow 6.

The fixation elements 41 are arranged at the lateral edges of the second lateral ends 12 and 22 of the first sheet 1 and the second sheet 2. The fixation element 42 is arranged at the top end 61 (the bottom end is marked with the number 62) of the sheets 1 and 2 and at the most inner meeting point 63 of the second lateral ends of the first sheet 1 and the second sheet 2. If the sheets are pulled back far enough to produce tension in the first sheet 1 and the second sheet 2, this will serve to hold the compression garment in place so that it does not fall down.

The fixation element 42 is arranged such that the second lateral end 12 of the first sheet 1 and the second lateral end 22 of the second sheet 2 are held together by the fixation element 42 directly at the leg 5 opposite to the straps 3. If desired, an additional fixation element 42a can be similarly placed at the bottom of the garment.

In FIG. 4 a cutting line 7 is marked by the marker 71. The cutting line 7 is marked on the garment and directly at the back side of the leg opposite to the straps 3. This is where the first sheet 1 and the second sheet 2 meet opposite to the straps at the position closest to the limb or the body part.

The cutting line 7 may only be marked on the second sheet 2. If the fitter does not have the capability of cutting both the first sheet 1 and the second sheet 2 simultaneously, the cutting line may be marked on the first sheet 1 and the second sheet 2.

In FIG. 5 the second sheet 2 lies on the first sheet 1 such that the first sheet 1 is not visible. The first sheet 1 and the second sheet 2 are cut with scissors 8 or a knife along the cutting line 7 over the full longitudinal length 64. The compression garment can be doffed for an easier cutting of the first sheet 1 and the second sheet 2

In FIG. 6 the compression garment is shown wherein the first sheet 1 and the second sheet 2 are cut open in two pieces and four cut ends 13, 14, 23, 24 are generated. The top or bottom edges 61 or 62 may be trimmed, if necessary, to fit the length of the limb. With other words, the longitudinal length 64 may be trimmed.

As shown in FIGS. 7a and 7b, the cut ends 13 and 23 are spliced together with a splicing element 9. The splicing element comprises a zip fastener 91. A strip with a loop surface 92 and 93 is sewn to each side of the zip fastener 91 and the zip fastener 91 is attached to the hook receptive outer surface of the first sheet 1 and the second sheet 2. To ease the assembly process, especially when the cut edges are contoured, the two sides of the zip fastener may be completely separated and each side of the zip fastener is applied individually along the cut edges 7 of the first sheet 1 and the second sheet 2.

The splicing element 9 is designed to be shorter than the compression garment because the longitudinal length 64 of the compression garment will vary, as the length of the compression garment can be cut down in length and the required splicing element length will vary if the seam is curved in shape. Therefore, both cut ends 13 and 23 are additionally spliced together by the fixation element 42 which is cut to width to fit the remaining length above the splicing element 9. A further fixation element 42 or 41 might be arranged below the splicing element.

Now, the compression garment is individually tailored and can be donned to the leg by detaching the releasable ends of straps 3 from the mating surfaces of the first sheet 1 or the second sheet 2. The straps 3 can be tightened in the direction of the arrow 34 such that the overlap between the strap 3 and the second sheet 2 is increased in order to establish compression to the leg.

If a reduction of edema occurs, the circumference of the leg decreases. The compression garment can be tailored again. For this, the straps 3 are adjusted to be in position providing the largest extension of the straps 3, the splicing element 9 is removed from the sheets 1 and 2, the lateral ends 12 and 22 are held together by arranging fixation elements 41 at the cut ends 13 and 23 and the tailoring of the compression garment is completed according to the further steps of the already disclosed method.

While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention shall not be limited to the particular embodiments disclosed, but that the invention will include all embodiments falling within the scope of the appended claims.

What is claimed is:

1. A method for tailoring a compression garment, the compression garment comprising:
  a first sheet and a second sheet, each having a first lateral end and a second lateral end, at least one strap for holding together the first lateral end of the first sheet and the first lateral end of the second sheet, wherein said at least one strap is tightenable to establish a compression level to a human limb or body part by the compression garment,
  the method including:
  a first step of adjusting the at least one strap to be in a first position;
  a second step of draping the compression garment around the limb or the body part;
  a third step of holding the second lateral end of the first sheet and the second lateral end of the second sheet together to pull the first sheet, the second sheet and the at least one strap into contact with said limb or body part, wherein the holding in the third step produces tension in the first sheet and the second sheet;

a fourth step of marking a cutting line on one or both sheets, wherein the fourth step occurs while the second lateral end of the first sheet and the second lateral end of the second sheet are being held together as a result of the third step;

a fifth step of cutting the first sheet and the second sheet along the cutting line; and a sixth step of splicing together both cut ends with at least one splicing element;

wherein the steps occur in the following chronological order: the first step, then the second step, then the third step, then the fourth step, then the fifth step, and then the sixth step.

2. The method of claim 1, wherein the second lateral end of the first sheet and the second lateral end of the second sheet are held together, such that lateral edges of the second lateral ends of the first sheet and the second sheet are aligned.

3. The method of claim 1, wherein the second lateral end of the first sheet and the second lateral end of the second sheet are held together by arranging at least one temporary releasable fixation element at lateral edges of the second lateral ends of the first sheet and the second sheet.

4. The method of claim 3, wherein at the sixth step both cut ends are additionally spliced together by at least one of the at least one fixation element or with another holding device.

5. The method of claim 1, wherein the second lateral end of the first sheet and the second lateral end of the second sheet are held together by arranging at least one fixation element at a top end and/or at a bottom end at a most inner meeting point of the second lateral end of the first sheet and the second sheet.

6. The method of claim 5, wherein at the sixth step both cut ends are additionally spliced together by at least one of the at least one fixation element or with another holding device.

7. The method of claim 1, wherein the second lateral end of the first sheet and the second lateral end of the second sheet are held together by arranging at least one fixation element directly at said limb or body part or at a small distance from said limb or said body part opposite to the at least one strap.

8. The method of claim 7, wherein at the sixth step both cut ends are additionally spliced together by at least one of the at least one fixation element or with another holding device.

9. The method of claim 7, wherein the small distance is at most 3 cm.

10. The method of claim 7, wherein the small distance is at most 1 cm.

11. The method of claim 7, wherein the small distance is at most 0.5 cm.

12. The method of claim 7, wherein the holding together of the second lateral end of the first sheet and the second lateral end of the second sheet occurs during the third step by arranging the at least one fixation element directly at said limb or body part or at the small distance from said limb or said body part opposite to the at least one strap.

13. The method of claim 1, wherein the cutting line is marked on the garment directly at said limb or body part opposite to the at least one strap, or at a small distance from the limb or the body part, opposite to the at least one strap, or where the first sheet and the second sheet meet opposite to the at least one strap at a position closest to the limb or the body part.

14. The method according to claim 13, wherein the small distance is at most 3 cm.

15. The method according to claim 13, wherein the small distance is at most 1 cm.

16. The method according to claim 13, wherein the small distance is at most 0.5 cm.

17. The method of claim 1, wherein a cumulated length of the first sheet, the second sheet, and the at least one strap is longer than a circumference of said limb or body part at the beginning of the first step.

18. The method of claim 1, wherein the at least one splicing element is attached on the first sheet and on the second sheet by hook-and-loop fasteners.

19. The method of claim 1, wherein the at least one splicing element comprises a slide fastener.

20. The method of claim 19, wherein the slide fastener is a zip fastener.

21. The method of claim 1, wherein the first sheet and the second sheet extend to a full longitudinal length of the compression garment.

22. The method of claim 1, wherein the first position is a position providing a largest extension of the at least one strap.

23. The method of claim 1, wherein the method comprises a further step before the first step, wherein the compression garment is pre-cut.

24. The method of claim 1, wherein the second lateral end of the first sheet and the second lateral end of the second sheet are held together by at least one temporary releasable fixation element.

25. The method of claim 1, wherein the fourth step of marking the cutting line occurs while the garment is in contact with the limb or the body part.

26. The method of claim 1, wherein the fifth step of cutting includes cutting the first and the second sheets, together or individually, along the cutting line, thereby creating two cut ends.

* * * * *